United States Patent
Carpenter

(10) Patent No.: US 12,295,819 B2
(45) Date of Patent: May 13, 2025

(54) ENHANCED WOMEN'S REUSABLE ABSORBENT PANTY

(71) Applicant: Jockey International, Inc., Kenosha, WI (US)

(72) Inventor: Michelle Frances Carpenter, Chicago, IL (US)

(73) Assignee: Jockey International, Inc., Kenosha, WI (US)

( * ) Notice: Subject to any disclaimer, the term of this patent is extended or adjusted under 35 U.S.C. 154(b) by 1113 days.

(21) Appl. No.: 17/103,122

(22) Filed: Nov. 24, 2020

(65) Prior Publication Data

US 2022/0160552 A1    May 26, 2022

(51) Int. Cl.
*A61F 13/49* (2006.01)
*A61F 13/15* (2006.01)
*A61F 13/537* (2006.01)

(52) U.S. Cl.
CPC .. *A61F 13/49006* (2013.01); *A61F 13/15268* (2013.01); *A61F 13/15577* (2013.01); *A61F 13/537* (2013.01); *A61F 2013/15878* (2013.01)

(58) Field of Classification Search
CPC ........ A61F 13/15; A61F 13/49; A61F 13/537; A61F 13/4906; A61F 13/494; A61F 13/56; A61F 13/66
See application file for complete search history.

(56) References Cited

U.S. PATENT DOCUMENTS

| | | | |
|---|---|---|---|
| 3,844,282 A | 10/1974 | King | |
| 4,560,381 A | 12/1985 | Southwell | |
| 4,956,878 A | 9/1990 | Boynton | |
| 6,353,940 B1 * | 3/2002 | Lyden | A41B 9/02 2/403 |

(Continued)

FOREIGN PATENT DOCUMENTS

| | | |
|---|---|---|
| CA | 119712 S | 4/2007 |
| CA | 117197 S | 8/2007 |

(Continued)

OTHER PUBLICATIONS

Mar. 15, 2022—(WO) International Search Report and Written Opinion—App PCT/US2021/072576.

(Continued)

*Primary Examiner* — Michele Kidwell
(74) *Attorney, Agent, or Firm* — Banner & Witcoff, Ltd.

(57) ABSTRACT

A reusable undergarment is disclosed with a multi-layer gusset assembly that is permanently affixed in the undergarment to absorb liquids excreted by a wearer of the undergarment and is reusable after washing. The panty also includes body fabric, elastic trim, and non-wicking hydrophobic thread that is sewn through the trim, which sandwiches the body fabric and gusset assembly. The trim may be a single piece of fabric with a waterproof finish that is folded widthwise to form a hollow channel that redistributes excess liquid at the edge of the gusset assembly without leaking. In some manufacturing processes, a waterproof (Continued)

100A

100B finish may be applied to the elastic trim, and the edge of the gusset assembly may be positioned offset from a fold-line of the trim when folded widthwise. The shape and positioning of the gusset assembly may be cone-shaped in some embodiments.

20 Claims, 13 Drawing Sheets

(56) References Cited

U.S. PATENT DOCUMENTS

| | | |
|---|---|---|
| 6,478,786 B1 | 11/2002 | Glaug et al. |
| 6,613,034 B2 | 9/2003 | Nozaki et al. |
| 6,782,557 B1 | 8/2004 | Feder |
| D500,131 S | 12/2004 | Choice |
| 6,895,603 B2 | 5/2005 | Coates |
| 7,081,036 B1 | 7/2006 | Howard et al. |
| D537,525 S | 2/2007 | Buchanan |
| 7,201,744 B2 | 4/2007 | Van Gompel et al. |
| D630,414 S | 1/2011 | Calabria |
| D632,055 S | 2/2011 | Wynn |
| D645,643 S | 9/2011 | Taylor |
| D649,330 S | 11/2011 | Trahin et al. |
| 8,117,675 B2 | 2/2012 | Strange et al. |
| D661,870 S | 6/2012 | Robles |
| D663,920 S | 7/2012 | Wexler |
| D663,921 S | 7/2012 | Wexler |
| D664,326 S | 7/2012 | Steele |
| 8,235,964 B2 | 8/2012 | Perneborn |
| 8,262,635 B2 | 9/2012 | Labit et al. |
| 8,292,868 B2 | 10/2012 | Schenck Mortell et al. |
| 8,361,049 B2 | 1/2013 | Coenen et al. |
| D677,447 S | 3/2013 | Shoemaker |
| D681,913 S | 5/2013 | Wexler |
| 8,460,265 B1 | 6/2013 | Calender |
| D685,156 S | 7/2013 | Carney et al. |
| D687,617 S | 8/2013 | Lacour-Phillippi |
| 8,499,364 B2 | 8/2013 | Dye |
| D690,898 S | 10/2013 | Wexler |
| D690,899 S | 10/2013 | Wexler |
| D690,900 S | 10/2013 | Wexler |
| D690,901 S | 10/2013 | Wexler |
| D690,902 S | 10/2013 | Wexler |
| D690,903 S | 10/2013 | Wexler |
| D692,208 S | 10/2013 | Lacour-Phillippi |
| D699,919 S | 2/2014 | Wexler |
| D699,920 S | 2/2014 | Wexler |
| D699,921 S | 2/2014 | Wexler |
| D701,018 S | 3/2014 | Wexler |
| D701,367 S | 3/2014 | Wexler |
| 8,672,916 B2 | 3/2014 | Brud et al. |
| D709,266 S | 7/2014 | Astin |
| D713,619 S | 9/2014 | Wexler |
| 8,834,441 B2 | 9/2014 | Coates |
| D716,020 S | 10/2014 | Dunbar et al. |
| 8,852,372 B2 | 10/2014 | Lakso et al. |
| D718,918 S | 12/2014 | Wexler |
| 8,935,813 B2 | 1/2015 | O'Leary |
| D724,818 S | 3/2015 | Wexler |
| D724,819 S | 3/2015 | Wexler |
| 8,968,266 B2 | 3/2015 | Kumar |
| D726,393 S | 4/2015 | Wexler |
| D741,045 S | 10/2015 | Scherr et al. |
| 9,198,805 B2 | 12/2015 | Gray et al. |
| D760,993 S | 7/2016 | Dawkins et al. |
| 9,572,726 B1 | 2/2017 | Ekstrom |
| D782,157 S | 3/2017 | Shoemaker |
| D782,158 S | 3/2017 | Shoemaker |
| D792,054 S | 7/2017 | Wexler |
| 9,700,079 B2 | 7/2017 | Franke et al. |
| D794,904 S | 8/2017 | Johnston |
| D799,153 S | 10/2017 | Astin |
| D800,301 S | 10/2017 | Ort |
| D810,398 S | 2/2018 | Kimel et al. |
| D811,041 S | 2/2018 | Bethke, Jr. |
| 9,962,286 B2 | 5/2018 | Mahon |
| D820,557 S | 6/2018 | Warman |
| D820,558 S | 6/2018 | Warman |
| D821,056 S | 6/2018 | Nezat et al. |
| 10,231,885 B2 | 3/2019 | Hovey |
| 10,244,798 B2 | 4/2019 | Wexler |
| 10,258,515 B2 | 4/2019 | Back et al. |
| 10,441,479 B2 | 10/2019 | Griffiths |
| 10,441,480 B2 | 10/2019 | Griffiths |
| 10,555,841 B2 | 2/2020 | Png et al. |
| D894,530 S | 9/2020 | Perry et al. |
| D915,736 S | 4/2021 | Karon |
| 11,154,431 B1* | 10/2021 | Yip ............... A61F 13/49006 |
| 2001/0025386 A1* | 10/2001 | Suga ................... A61F 13/72 2/406 |
| 2004/0230175 A1 | 11/2004 | Rainville-Lonn et al. |
| 2008/0103471 A1* | 5/2008 | LaVon ............ A61F 13/505 604/385.19 |
| 2009/0299311 A1 | 12/2009 | Deerin |
| 2011/0094017 A1 | 4/2011 | Strange et al. |
| 2011/0172621 A1 | 7/2011 | Lee et al. |
| 2011/0265255 A1 | 11/2011 | Hyndman |
| 2014/0025027 A1 | 1/2014 | Png et al. |
| 2014/0039432 A1 | 2/2014 | Dunbar et al. |
| 2016/0089276 A1 | 3/2016 | Griffiths |
| 2016/0296384 A1 | 10/2016 | Png et al. |
| 2017/0231834 A1 | 8/2017 | Sang |
| 2018/0325746 A1 | 11/2018 | Newson |
| 2019/0328047 A1 | 10/2019 | Beach et al. |
| 2020/0000155 A1 | 1/2020 | Etienne |
| 2020/0297556 A1* | 9/2020 | Png ............... A61F 13/49006 |
| 2021/0290447 A1* | 9/2021 | Sepello ............ A61F 13/15268 |
| 2022/0211558 A1* | 7/2022 | Kajanthan ......... A61F 13/49453 |

FOREIGN PATENT DOCUMENTS

| | | |
|---|---|---|
| CA | 133058 S | 6/2010 |
| CA | 134304 S | 9/2010 |
| CA | 2720569 A1 | 5/2012 |
| CA | 146804 S | 1/2013 |
| CA | 147605 S | 8/2013 |
| CA | 147606 S | 8/2013 |
| CA | 2827795 A1 | 11/2013 |
| CA | 143769 S | 12/2013 |
| CA | 2961668 A1 | 3/2015 |
| CA | 2945296 A1 | 10/2015 |
| CA | 176845 S | 3/2018 |
| EP | 0033569 A2 | 8/1981 |
| KR | 950000152 U | 1/1995 |

OTHER PUBLICATIONS

Apr. 18, 2023 (WO) International Preliminary Report on Patentability Chapter II—App PCT/US2021/072576.
Sep. 23, 2024—(EP) European Search Report—App EP21899260.0.

* cited by examiner

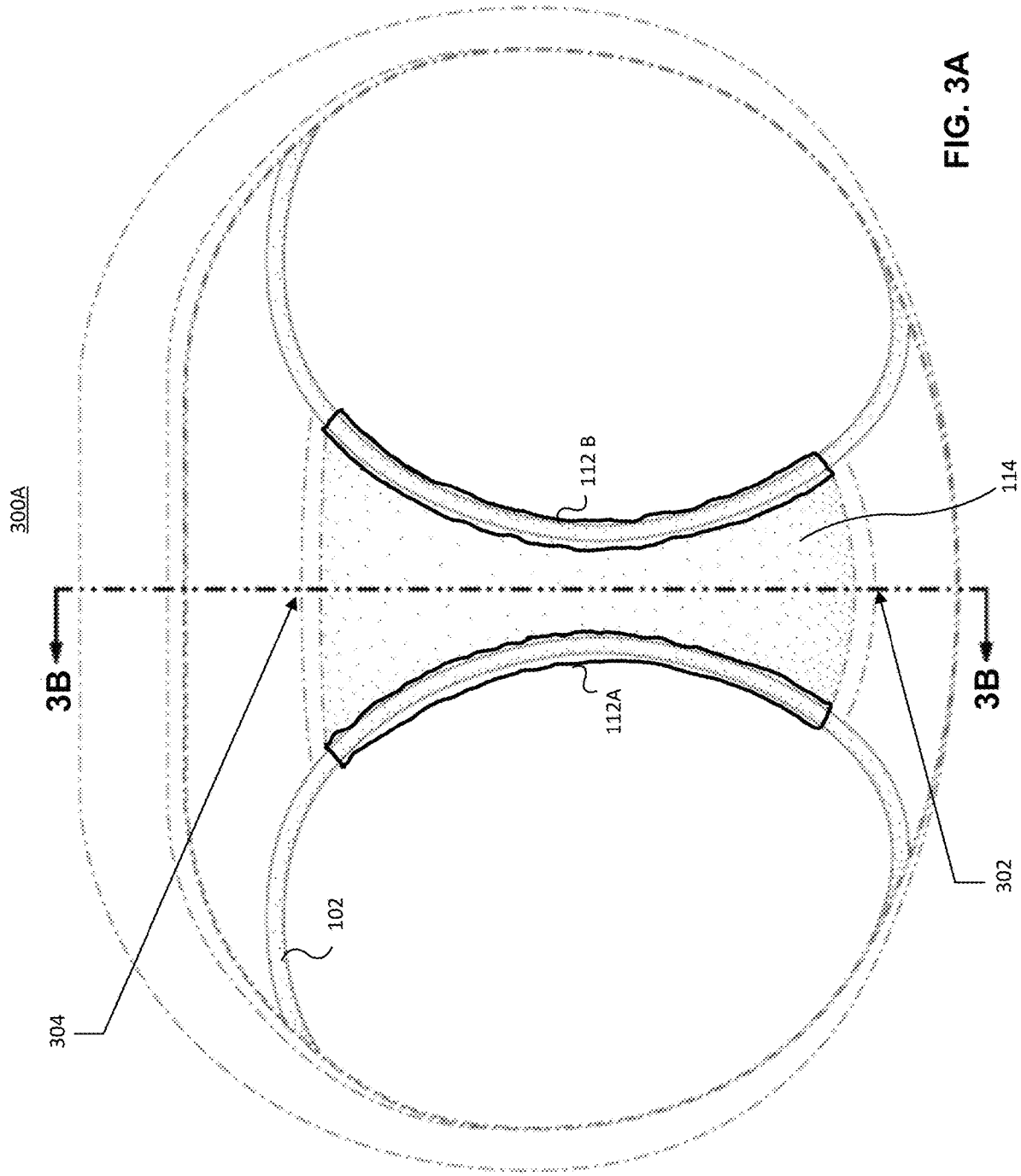

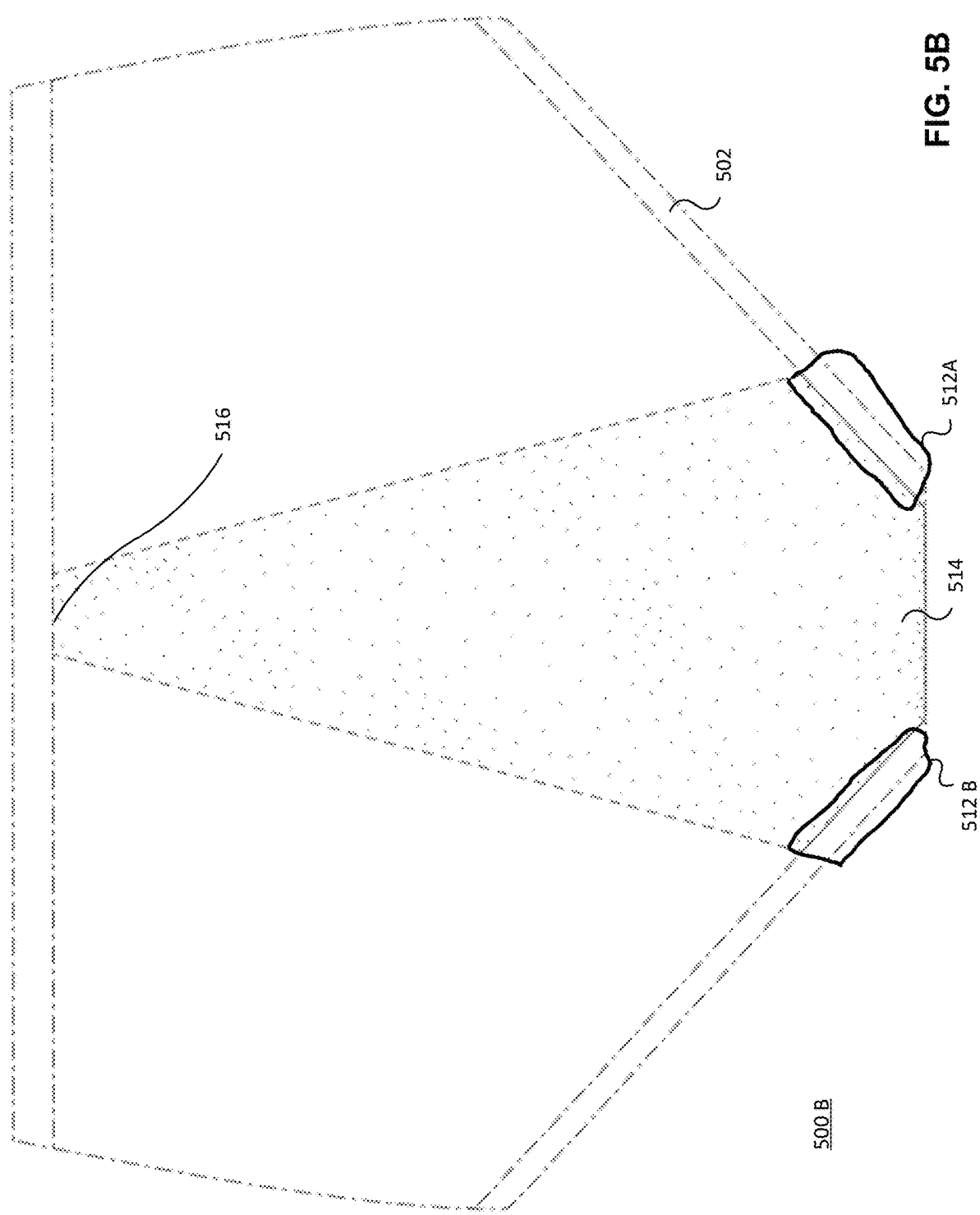

ENHANCED WOMEN'S REUSABLE ABSORBENT PANTY

CROSS-REFERENCE TO RELATED APPLICATIONS

This application does not claim the benefit of priority to any earlier-filed application.

This application is related to U.S. Design patent application Ser. No. 29/759,634, which was concurrently filed with this application on Nov. 24, 2020.

This application is related to U.S. Design patent application Ser. No. 29/759,641, which was concurrently filed with this application on Nov. 24, 2020.

This application is related to U.S. Design patent application Ser. No. 29/759,644, which was concurrently filed with this application on Nov. 24, 2020.

And, all three of the aforementioned design patent applications are herein incorporated by reference in their entireties.

BACKGROUND

Although undergarment leaks may occur at any time, women experience them more often during the initial days of their menstrual cycle. Some undergarments claim to solve the issue of menstrual leaks. However, they have various shortcoming that remain unaddressed. For example, some use barrier fabrics that are aesthetically unpleasing, uncomfortable, environmentally unfriendly, or not suitable for use as an undergarment for daily use. The embodiments disclosed herein overcome one or more shortcomings in the art.

SUMMARY

The following summary presents a simplified summary of certain features. The summary is not an extensive overview and is not intended to identify key or critical elements. An article of manufacture is described with a multi-layer gusset assembly that is permanently affixed in the undergarment to absorb liquids excreted by a wearer of the undergarment and is reusable after washing. The panty also includes body fabric, elastic trim, and non-wicking hydrophobic thread that is sewn through the trim, which sandwiches the body fabric and gusset assembly. The trim may be a single piece of fabric with a waterproof finish that is folded widthwise to form a hollow channel that redistributes excess liquid at the edge of the gusset assembly without leaking.

One general aspect includes a method of manufacturing/assembling an undergarment with a gusset assembly. In some manufacturing processes, a waterproof finish may be applied to an elastic trim, and the edge of the gusset assembly may be positioned offset from a fold-line of the trim when folded widthwise. The shape and positioning of the gusset assembly may be cone-shaped in some embodiments. One or more other steps (or different steps) may be performed by the aforementioned method.

While aspects of the disclosure have been described in terms of illustrative embodiments thereof, it should be understood by those skilled in the art that various changes may be made and equivalents may be substituted for elements thereof without departing from the scope of the disclosure. Numerous other embodiments, modifications, and variations within the scope and spirit of the appended claims will occur to persons of ordinary skill in the art from a review of this disclosure.

BRIEF DESCRIPTION OF THE DRAWINGS

The foregoing summary, as well as the following detailed description of exemplary embodiments, is better understood when read in conjunction with the accompanying drawings, which are included by way of example, and not by way of limitation with regard to the claimed invention.

FIG. 3A and FIG. 3B (collectively referred to as "FIG. 3") show different views of an example of a light coverage, reusable panty, in accordance with one or more embodiments.

FIG. 5A and FIG. 5B (collectively referred to as "FIG. 5") show different views of an inside out configuration of an example of a full coverage, reusable panty, in accordance with one or more embodiments.

DETAILED DESCRIPTION

Figure 1A:
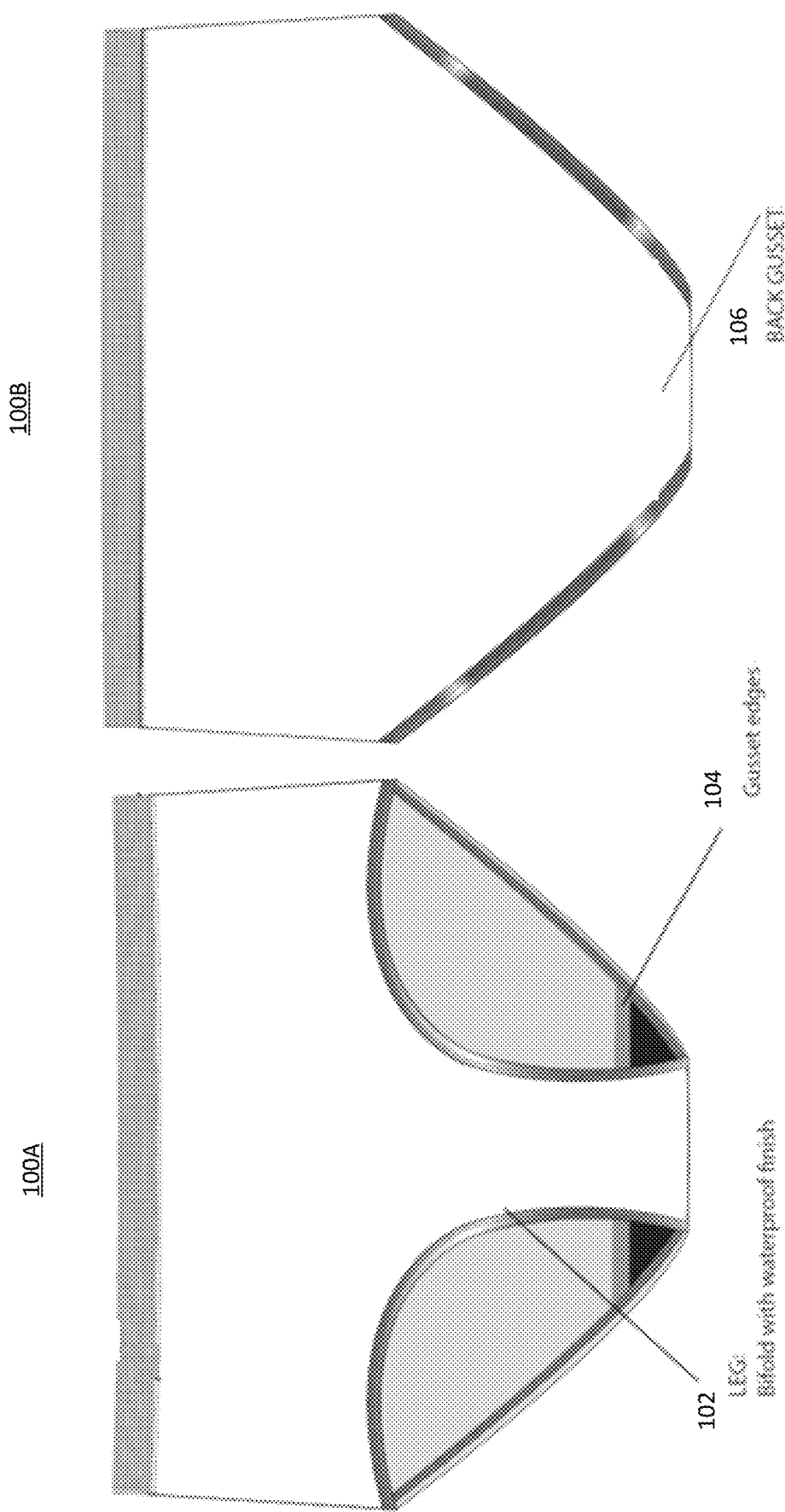
FIG. 1A, FIG. 1B, and FIG. 1C (collectively referred to as "FIG. 1") show an example of a light coverage, reusable panty, in accordance with one or more embodiments.

In one example, a woman's absorbent (e.g., leak-resistant) undergarment is disclosed. The undergarment may be a reusable, washable leak-resistant undergarment that is designed to deal with leakages related to menstruation, spotting, post-partum, discharge, incontinence, and/or sweat. The illustrative undergarment may provide a modernized version of single-use disposable underwear such as incontinence garments and adult diapers that provide an aesthetically pleasing, cost-effective, and environmentally friendly solution to leakage issues. Although some examples of the undergarment might not server as a replacement for pads, tampons, menstruation cups, etc., they may supplement and provide additional leakage protection during light and heavy flow/discharge days, when used for that specific application.

In some examples, a reusable undergarment is disclosed with a multi-layer gusset assembly that is permanently affixed in the undergarment to absorb liquids excreted by a wearer of the undergarment and is reusable after washing. In some examples, the panty also includes body fabric, elastic trim, and non-wicking hydrophobic thread that is sewn through the trim, which sandwiches the body fabric and gusset assembly. The trim may be a single piece of fabric with a waterproof finish that is folded widthwise to form a hollow channel that redistributes excess liquid at the edge of the gusset assembly without leaking.

While aspects of the disclosure contemplate an illustrative undergarment that provides superior fit with a full coverage seat that protects against liquid with a high level of discretion, the appropriate level of protection may be varied in different examples. For example, the disclosure contemplates women's brief s that include: light coverage, moderate coverage, full coverage, and other varying levels of coverage. Meanwhile, the aforementioned undergarments may further include enhanced features such as: no/minimal noise, no seepage to body fabrics, no/minimal malodor, and/or no/minimal excess bulk. The aforementioned undergarments provide a better wearing experience by offering full seat coverage fit, protection in the appropriate regions without fear of bleed-through (e.g., via various construction options), and/or superior liner fabrication. In one example, the aforementioned undergarment may include a leak-proof padding with a design and functionality that is novel and nonobvious. In another example, the aforementioned undergarment may include a construction and placement of a padded gusset within the undergarment that has a design and functionality that is novel and nonobvious.

In one example, a reusable undergarment is disclosed comprising an assembly of body fabric, a gusset assembly, trim, and hydrophobic thread. The body fabric may comprise a continuous waistband and two leg opening portions through which a person's legs would be placed. In some examples, the body fabric in contact with the trim is void of any visible pleats or folds (e.g., as are common around the leg opening of a baby's diaper) in the body fabric running generally perpendicular to the trim. Moreover, the gusset assembly may comprise multiple layers (e.g., more than two layers) and may be positioned inside the undergarment. In one example, the gusset assembly may be permanently affixed in the undergarment to absorb liquids excreted by a wearer of the undergarment and is reusable after washing. In other words, the woman's panty embodiment includes an absorbent layer that is permanently sewn into the inside crotch area of the panty without the ability to insert and remove the absorbent layer. The gusset assembly may include at least an absorbent layer, wicking layer, and water-resistant shield layer, in some examples.

The trim on the reusable garment may be an elastic trim to provide comfort and to hold in place when a wearer is walking or moving. With undergarments that have a total of two leg openings, the gusset assembly is positioned between the two leg openings so that the second edge of the gusset assembly is opposite the first edge of the gusset assembly. A first bi-fold, elastic trim may sandwich a first of the two leg opening portions and a first edge of the gusset assembly; likewise, a second bi-fold, elastic trim may sandwich a second of the two leg opening portions and a second edge of the gusset assembly. In particular, as explained herein, because of the integration of thread for the sandwiching performed by the first bi-fold, elastic trim, the sandwiching may be performed in the absence of any of chemical bonding, elastic bonding film, thermal-compression bonding, or combination thereof. In addition, in some examples, the bi-fold, elastic trims may each be a single piece of fabric with a waterproof finish. And, the elastic trim may be folded widthwise to form a channel in which to collect and redistribute excess liquid at the edges of the gusset assembly without leaking out onto an outer apparel of the wearer of the undergarment.

The sandwiching of the bi-fold trim may be performed with a first non-wicking and/or hydrophobic thread sewn through the first bi-fold trim and all of the layers of the gusset assembly. Likewise, a second non-wicking and/or hydrophobic thread may be sewn through the second bi-fold trim and all of the layers of the gusset assembly to form the sandwiching by the second bi-fold trim. In some examples, the thread may be sewn through less than all of the layers and sub-layers of the gusset assembly when affixing to the first and second bi-fold trims, so long as the thread penetrates through the overall gusset assembly to affix it to the undergarment. In some examples, the undergarment is assembled with a first thread and second thread that are separate threads to avoid having to span the gap between the two leg openings. However, in other examples, the first and second thread may be a single thread that is integrated into the undergarment.

While several examples refer to enhancements to a woman's undergarment, the disclosure is not so limited. Rather, other examples of the enhancements disclosed herein may be adapted and incorporated into other apparel for women, such as maternity bras, men's non-menstrual reusable briefs for incontinence, unisex t-shirts with absorbent underarm pads, and other apparel products. In addition, the undergarment may be styled as a low-rise panty, high cut/French cut, hipster, bikini, boy-short, brief, tanga brief, control brief, or other styled undergarment. Moreover, the body fabric (e.g., outer layer fabric) of the apparel may be made from a multi-direction stretchable fabric such as spandex, cotton, cotton blend, or other material. Furthermore, additional features/enhancements are also contemplated by this disclosure. For example, an antimicrobial yarn or nature-based treatment may be used for the absorbent layer (e.g., gusset assembly); and a TPU liner that is resistant to liquid but not gas for breathability may be used in construction of the gusset assembly.

A non-exhaustive list of benefits and/or advantages of the novel and non-obvious features disclosed herein include but are not limited to: preventing leaks by wicking liquid away from the body and storing it in an absorbent layer, providing comfort while wearing the product and security throughout use, reducing waste caused by single use hygiene products, and/or reducing consumer cost over time. While the absorbent layer disclosed herein is designed to store liquids excreted by a wearer, the absorbent layer was not purposed designed with an elastic water-repellent polymer that holds (e.g., with hydrostatic pressure resistance) liquid only up to a threshold ML capacity, but then releases the liquid once that specific capacity is exceeded. Doing so would result in an untimely and unsightly release of a noticeable amount of liquids onto the outer clothing of a wearer.

Figure 1B:
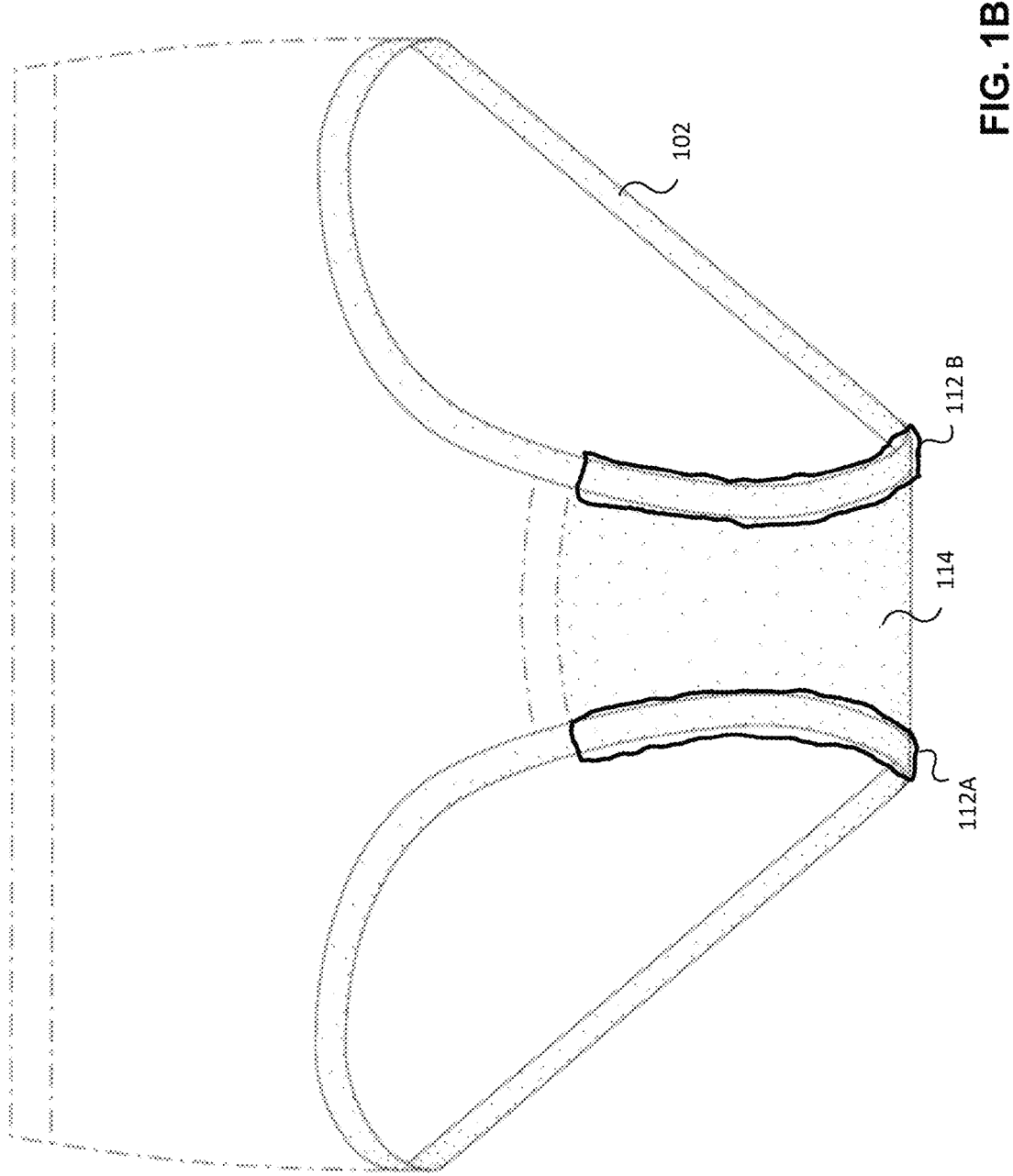
Figure 1C:
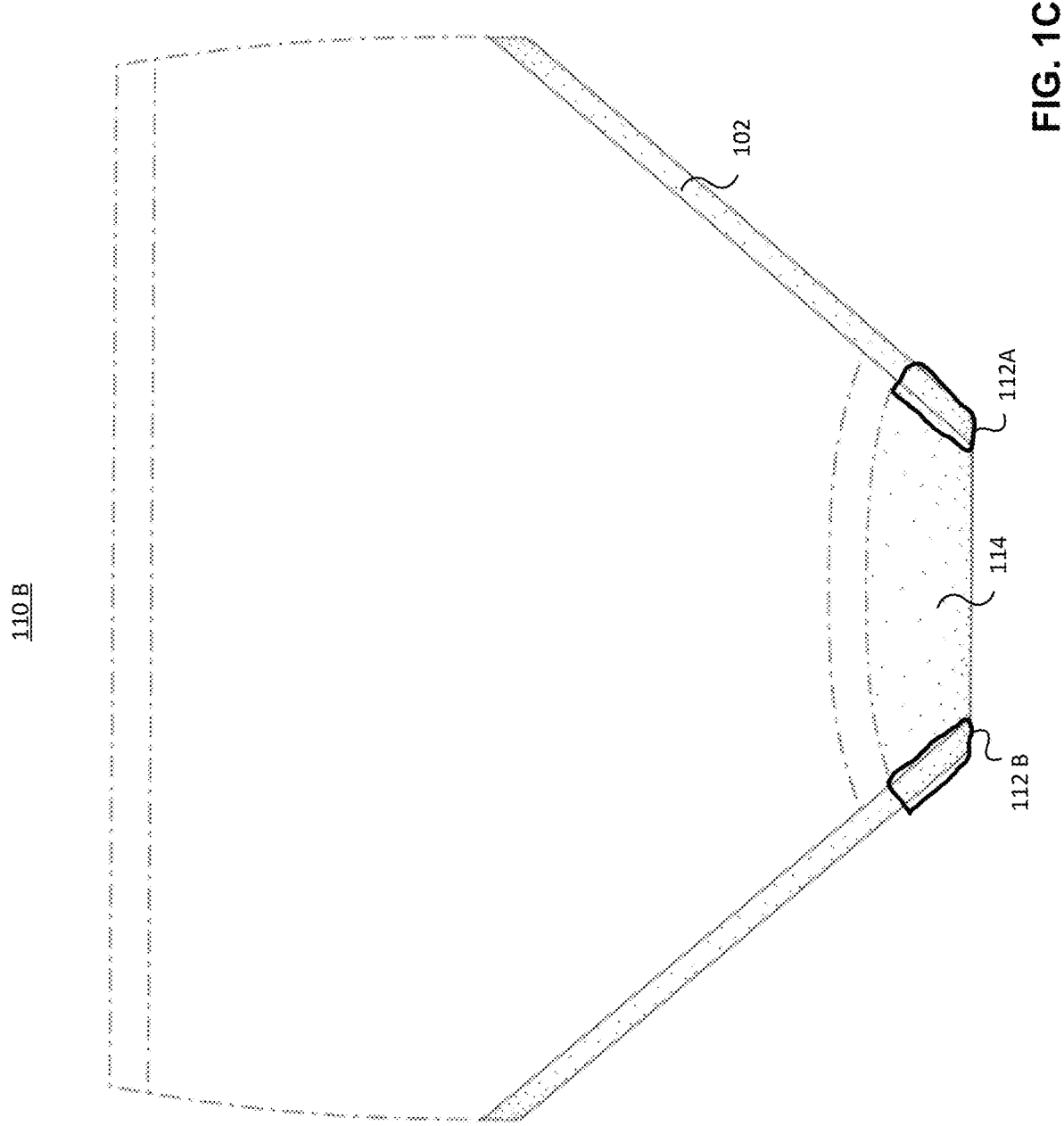

FIG. 1A, FIG. 1B, and FIG. 1C (collectively referred to as "FIG. 1") show an example of a light coverage, reusable panty, in accordance with one or more embodiments. FIG. 1A shows a front view 100A and back view 100B of an illustrative rendering of a light coverage, reusable panty, in accordance with one or more embodiments. The leg opening portion 102 of a first leg of the panty includes a bi-fold trim that follows the circumference of the leg opening. A second leg opening portion is also displayed with a bi-fold trim assembled on it. A gusset assembly is positioned inside the undergarment with the edges 104 of the gusset assembly sandwiched between the trim. Two edges of the gusset assembly are sandwiched between the two trims on each leg opening. Meanwhile, other edges of the gusset assembly, such as the top and bottom of the gusset assembly as oriented in FIG. 1, may be affixed to the body fabric of the undergarment using any one or more of various means. However, from the outside, the back of the illustrative panty in FIG. 1A does not have visible stitching on the outside of the panty running horizontally from one leg opening to the other where the back 106 of the gusset would be affixed—the panty has minimal visual cues from the outside of the garment. For example, the panty in FIG. 1A does not have visible stitching on the outside rear of the panty that forms a largely triangular shape.

In addition, the undergarment 100A, 100B in some examples has a continuous waist band that is unobstructed by any fastener, Velcro-release, releasable belt, buckle, or such. While the waist band depicted in FIG. 1A is a basic rectangular band, in some examples, the top of the waist band may include ornamental edge designs such as a scalloped or rounded design. In some examples, the aforementioned design may be lace or lace-like. However, the waist band does not have a scalloped/rounded edge design at both the top and bottom edge of the waist band, as illustrated in FIG. 1A.

FIG. 1B shows a front view of an inside out, flat configuration 110A of an example of the light coverage, reusable panty from FIG. 1A, in accordance with one or more embodiments. A gusset assembly 114 is positioned inside the undergarment with the edges of the gusset assembly sandwiched between the two trims on each leg opening. The two regions 112A, 112B where the two opposing edges of the gusset assembly are sandwiched between the two trims on each leg opening may be held together using any of various means. In one embodiment, a thread may be sewn through the aforementioned pieces to assemble the reusable panty in FIG. 1B. In some embodiments, the thread may be a non-wicking thread and/or a thread with hydrophobic properties or additives/agent that further the waterproof characteristics of the trim. In some examples, thread may be used in region 112A, 112B, but a different means (e.g., adhesive, chemical bonding, elastic bonding film, thermal-compression bonding, or combination thereof) may be used for the remainder of the trim that runs along the leg opening. In other examples, the entirety of the trim circling the two leg openings may be sewn to affix the trim to the appropriate pieces.

Various types of stitching and thread may be used in the various illustrative garments described in this disclosure, including that of FIG. 1. Specifically, stitching may be used in region 112A, 112B of the trim in FIG. 1. In one example, a two-needle cover stitch may be used to affix the trim and gusset assembly together. In other examples, another stitch type appropriate for an elastic material assembly may be used and would be apparent to a person having ordinary skill in the art after review of the entirety disclosed herein. Some examples of stitch types known in the art include, but are not limited to a straight stitch, triple straight stitch, zigzag stitch, three step zigzag, lightning bolt stitch, honeycomb stitch, overlock/overedge stitch, feather stitch, or combination thereof. For example, a straight stitch is frequently used when paired with a thread having stretch/stretchability characteristics; meanwhile, a honeycomb stitch is often used for attaching elastic or stretch lace or other similar material. In addition, a triple straight stitch (e.g., backstitch, stretch stitch, triple stretch stitch, etc.) is often used as a seam for tight garments and hemming; it is made by the needle going two stitches forward and one stitch back, thus making a stronger seam for crutch seams, armscyes, and the like. The triple straight stitch is also often used for sewing stretch fabrics because it prevents/reduces snap when stretched. Finally, a zigzag stitch may be used for finishing raw edges, while an overlock/overedge stitch, lightning bolt stitch (e.g., stretch stitch), and/or three step zigzag are sometimes used for main construction seams. The aforementioned is merely an abbreviated list that is not meant to be exhaustive of all stitches and thread types contemplated by this disclosure. A person of skill in the art after review of the entirety disclosed herein will appreciate that other stitches and thread types are contemplated by the disclosure.

FIG. 1C shows a back view of an inside out, flat configuration 110B of the light coverage, reusable panty in FIG. 1B, in accordance with one or more embodiments. Notably, while two edges of the gusset assembly are sandwiched using thread through the trim (e.g., elastic trim) at the leg openings 102, the other edges of the gusset assembly, such as the top and bottom of the gusset assembly, may be affixed to the body fabric of the undergarment using any one or more of various means. For example, the dot-dashed line across the panty in FIG. 1B from one leg opening to the other leg opening may be a tape or other material that bonds the gusset assembly to the body fabric of the panty. In any event, when viewed from the outside, the back of the illustrative panty in FIG. 1C does not have visible stitching along the dot-dashed line. In various embodiments, even when a waterproof tape is used at the top and/or bottom of the gusset assembly in FIG. 1C, the waterproof tape does not come in contact with the leg opening region of the panty's body—rather, a small gap is provided for between the edge of the waterproof tape and the leg opening. In other words, no part of the bi-fold trim is bonded to another surface using any type of adhesive bond or elastic bonding film, in that particular embodiment.

Figure 2:
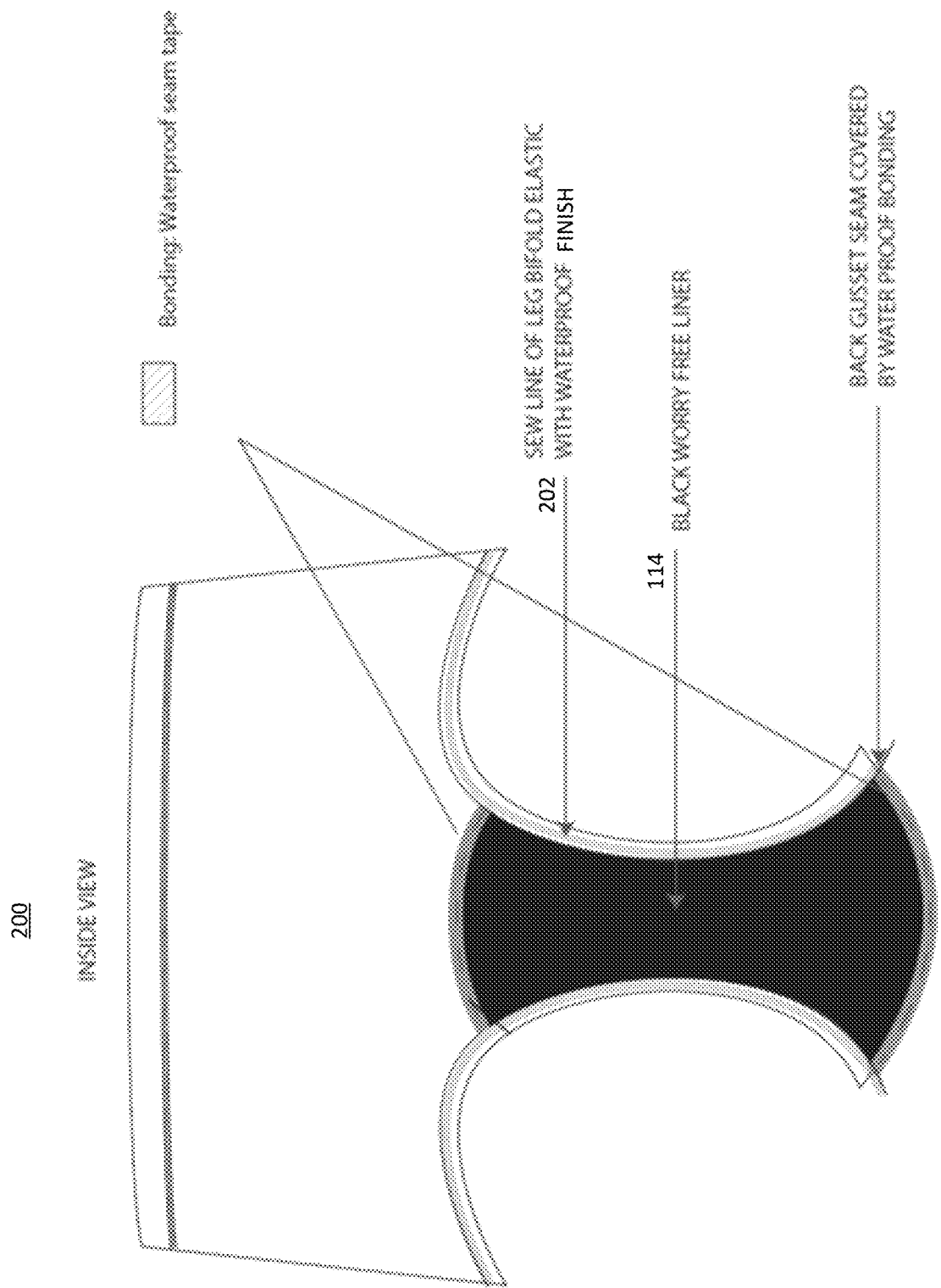
FIG. 2 shows an inside construction of an example of a moderate coverage, reusable panty, in accordance with an embodiment.

FIG. 2 shows an inside construction 200 of an example of a moderate coverage, reusable panty, in accordance with an embodiment. The inside view shows the material of an undergarment laid open. The dark area 114 is an illustrative gusset assembly, which in this example is colored black, however may be other colors in other examples. In particular, the edge of the gusset assembly 114 is sandwiched with a sew line 202 on the bi-fold trim around the leg opening of the undergarment. In one example, a non-wicking, hydrophobic thread is sewn through the bi-fold trim and the layers of the gusset assembly to form the sandwiching by the bi-fold trim. In one example, the undergarment uses a bi-fold trim sewn along the circumference of the leg opening of the panty using a waterproof thread and without any adhesive or bonding film inside the trim. In other words, the sandwiching by the bi-fold, elastic trim is done in the absence of any of chemical bonding, elastic bonding film, thermal-compression bonding, or combination thereof. The same is performed for the other leg opening of the undergarment. In some examples, the thread on a first leg opening and the thread on a second leg opening are separate threads.

The gusset assembly 114 in FIG. 2 shows a waterproof seam tape that joins one or more layers of the gusset assembly to the body fabric of the panty at the top and bottom edge of the gusset as oriented in FIG. 2. The waterproof tape is positioned so that it does not come in contact with the leg opening region of the panty's body—in other words, a small gap (e.g. separation) remains between the edge of the waterproof tape and the edge of the gusset assembly that is sandwiched between the trim. In one example, the gap in the waterproof tape is in the region immediately along the circumference of the leg opening between the sewn area and the leg opening.

Figure 3B:
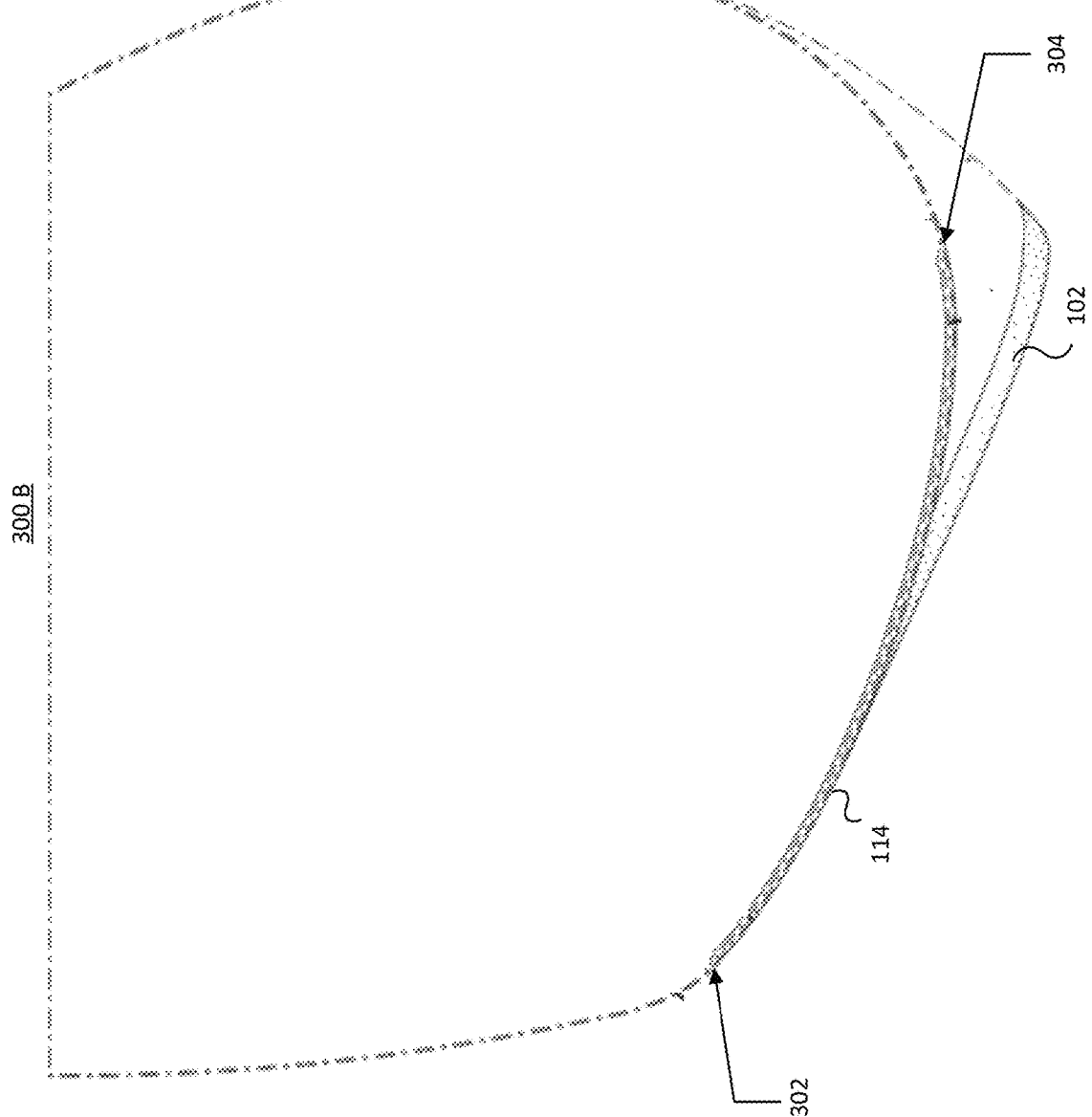

FIG. 3A and FIG. 3B (collectively referred to as "FIG. 3") show different views of an example of a light coverage, reusable panty, in accordance with one or more embodiments. FIG. 3A shows a bottom view 300A of an in-use configuration of an example of a light coverage, reusable panty, in accordance with one or more embodiments. The top edge 302 and bottom edge 304 of the gusset assembly 114, as reference in earlier figures, may be affixed to the body fabric of the undergarment with adhesive, bonding, or other techniques. Meanwhile, the regions 112A, 112B of the elastic trim are affixed to the undergarment with a waterproof, sewn thread. The dot-dashed line bisecting the undergarment denotes a cross-section line referencing FIG. 3B.

In one example, the undergarment (e.g., panty) is designed to provide an absorbent and leak-proof panty while solving for concerns around discretion and comfort. The panty provides superior fit with a full coverage seat (e.g., not a thong-style panty) and appropriate levels of protection against liquid with a high level of discretion. The panty prevents leaks by wicking liquid away from the body and storing it in an absorbent layer in the gusset assembly. The panty construction includes an elastic trim that is folded (i.e., bi-fold) and affixed to assist with collecting and redistributing excess liquid at the edge of the gusset assembly without leaking out onto an outer apparel of the wearer of the panty. The trim forms a channel that holds in any excess liquid spilling out from the corresponding edge of the gusset assembly and spreads it to other regions of the gusset assembly in contact with the channel. When these other regions of the gusset are less saturated than the regions of the gusset from where excess liquid is spilling out, they may absorb the excess liquid and distribute it to less saturated regions of the gusset assembly. Therefore, the overall ability of the undergarment to prevent leaking out behavior is improved.

FIG. 3B shows a cross-section view 300B of the light coverage, reusable panty in FIG. 3A, in accordance with one or more embodiments. The cross-section view makes clear that in some illustrative light coverage, reusable panties, the top edge 302 of the gusset assembly 114 may be forward and higher than the bottom edge 304 of the gusset assembly. Moreover, the gusset assembly 114, as explained in FIG. 7, has an illustrative thickness/depth that is depicted in this cross-section view. Of course, the thickness/depth of the gusset assembly 114 varies depending on the number of layers, type of fabrics/materials, and other factors. While some embodiments refer to a gusset assembly with three layers, the disclosure is not so limited and contemplates embodiments where the gusset assembly comprises just two layers, four layers, or even more layers or sublayers.

Figure 4:
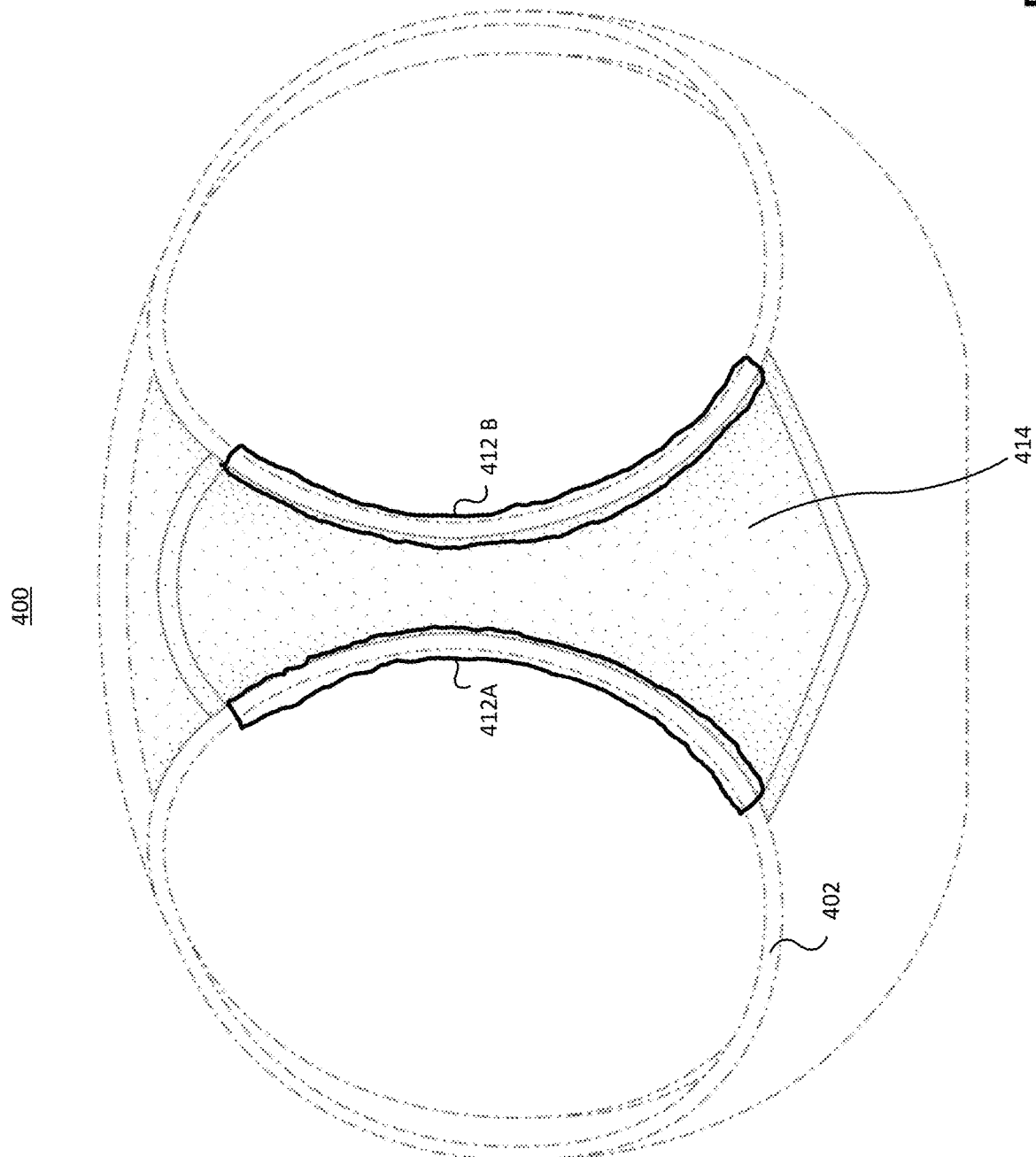
FIG. 4 shows a bottom view of an inside out, in-use configuration of an example of a moderate coverage, reusable panty, in accordance with one or more embodiments.

FIG. 4 shows a bottom view 400 of an inside out, in-use configuration of an example of a moderate coverage, reusable panty, in accordance with one or more embodiments. Like the light coverage undergarment in FIG. 3A, the elastic trim 402 in the illustrative moderate coverage, reusable panty in FIG. 4 covers the region around the leg opening of the undergarment. Noticeably, the shape and other characteristics of the gusset assembly 414 may be different in a moderate coverage panty. For example, the bottom edge of the gusset assembly 414 has a more triangular, shallow cone-like shape. The modified shape of the gusset assembly 414 may provide greater coverage and protection from leaks. Meanwhile, similar to FIG. 3A, a moderate coverage undergarment also includes regions 412A, 412B of the elastic trim that are affixed to the undergarment with a sewn thread (e.g., a non-wicking and waterproof thread, or other thread). As previously elaborated herein, the sewn thread may extend past regions 412A, 412B of the trim to the remainder of the trim.

Figure 5A:
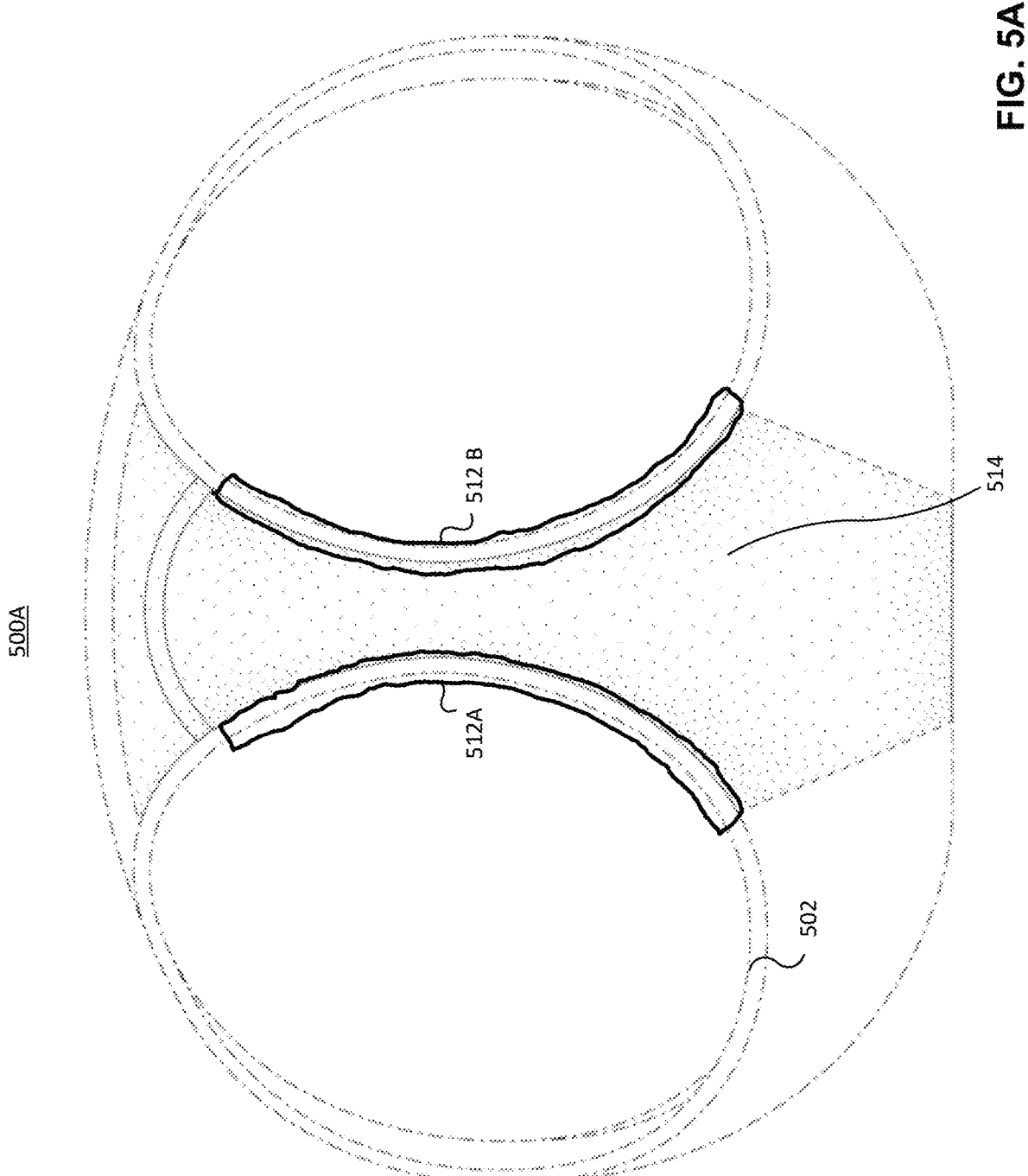

FIG. 5A and FIG. 5B (collectively referred to as "FIG. 5") show different views of an inside out configuration of an example of a full coverage, reusable panty, in accordance with one or more embodiments. In particular, FIG. 5A shows a bottom view 500A of an inside out, in-use configuration of an example of a full coverage, reusable panty, in accordance with one or more embodiments. Like a light coverage undergarment in FIG. 3A and a moderate coverage undergarment in FIG. 4, the elastic trim 502 in the illustrative full coverage, reusable panty in FIG. 5 covers the region around the leg opening of the undergarment. Although FIG. 5 shows a trim running the full circumference of the leg opening of the undergarment, in some examples, the trim may primarily reside in the area denoted in 512A, 512B to assist in affixing a liner to the undergarment; the trim may extend past the area denoted in 512A, 512B in some examples to extend along more of the circumference of the leg opening without extending over the full circumference.

Noticeably, in FIG. 5B, the shape and other characteristics of the gusset assembly 514 may be different in a full coverage panty. For example, the bottom edge of the gusset assembly 514 has an even more triangular and cone-like shaped than the shape of the gusset assembly 414 in FIG. 4. The modified shape of the gusset assembly 514 may provide greater coverage and protection from leaks. The rear view 500B, shown in FIG. 5B, of the inside out, flat configuration of the full coverage, reusable panty in FIG. 5A illustrates that in some examples, the gusset assembly 514 may be a cone-shaped portion spanning from a crotch region between the two leg opening portions all the way up to the continuous waistband 516, wherein a narrowest end of the cone-shaped portion contacts the continuous waistband. Notably, the illustrated gusset region in FIG. 5 is narrower in the buttock region than in the crotch region. Although the disclosure contemplates that the gusset assembly may be positioned in the inside of the undergarment at various positions according to desired coverage configuration, the positioning of the apex of the crotch region of the gusset assembly is not such that it is closer to the front-end waistband compared to the center fold line of the panty crotch region. In addition, similar to FIG. 3A and FIG. 4, a full coverage undergarment may also include regions 512A, 512B of the elastic trim that are affixed to the undergarment with a waterproof, sewn thread, in some examples. In an alternate embodiment, a full coverage undergarment may have regions 512A, 512B of the elastic trim that are affixed to the undergarment without sewn thread—rather they are affixed with bonding, adhesive, tape, or other method. In the aforementioned reusable panty with full coverage, the additional regions of the gusset assembly 514 in the rear of the panty further protect from leaks and wetness.

Figure 6:
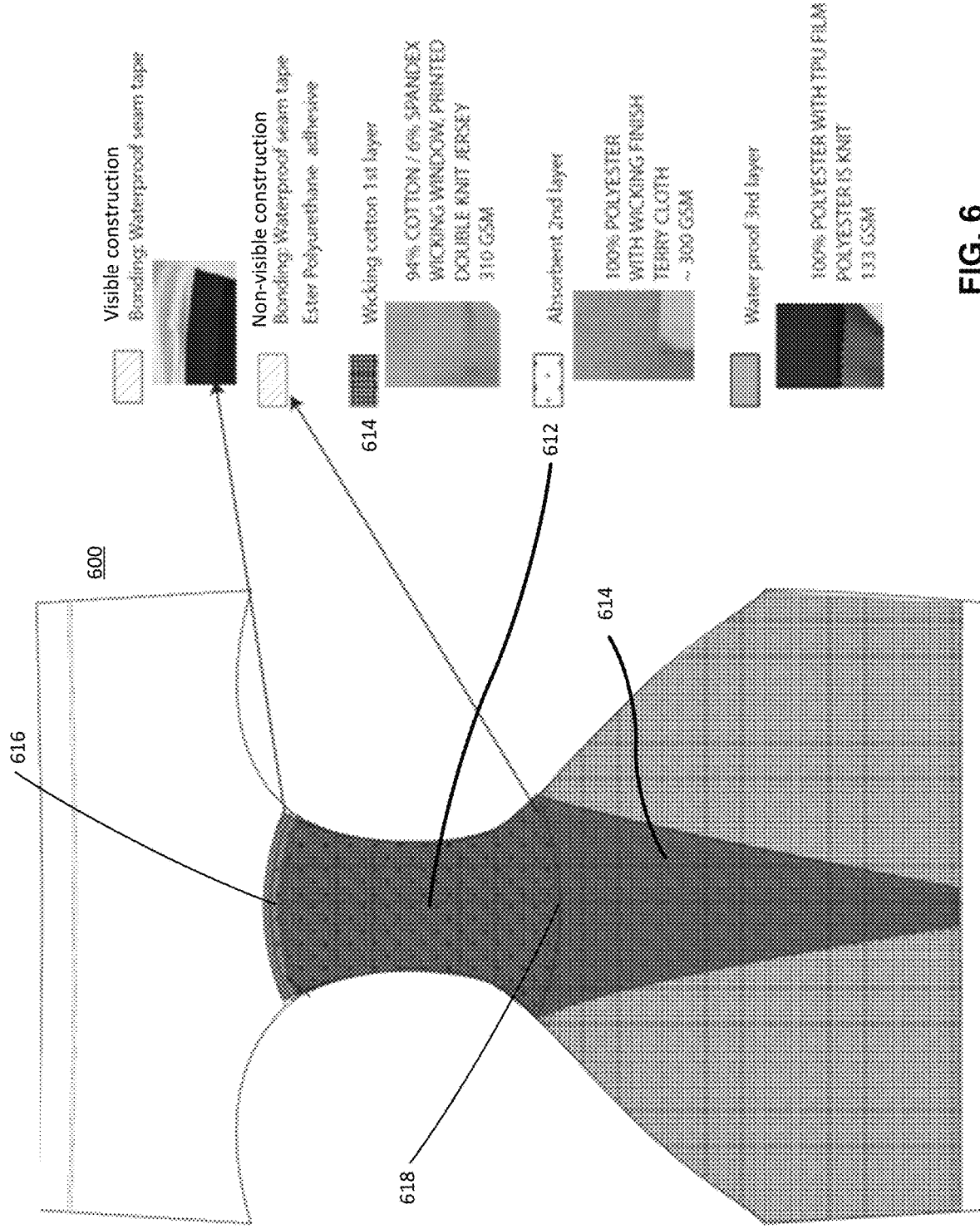
FIG. 6 shows an inside construction of an example of a full coverage, reusable panty, in accordance with an embodiment.

FIG. 6 shows an inside construction 600 of an illustrative full coverage, reusable panty, in accordance with an embodiment. In one example, a reusable undergarment in FIG. 6 may use waterproof seam tape 616 to join the gusset assembly to the body fabric of the panty at the top edge of the gusset, and waterproof seam tape 618 to join one or more layers of the gusset assembly to the body fabric of the panty at the bottom edge of the gusset. While tape 616 is visible when viewing the fully-constructed panty, tape 618 is not visible because wicking layer 614 of the gusset assembly is covering the tape 618. In any event, the tape 616, 618 is positioned so that it does not come in contact with the leg opening region of the panty's body—in other words, a small gap (e.g., separation) remains between the edge of the waterproof tape 616, 618 and the edge of the gusset assembly that is sandwiched between the trim. In an alternate embodiment involving a reusable panty with less than full coverage, such as illustrated in FIG. 2, a waterproof seam tape may be used to join the entire gusset assembly 114 to the body fabric at both the top edge and bottom edge of the gusset. The aforementioned reusable panty might not extend as much upwards in the rear of the panty, thus its comparable, first layer 614 may terminate at about the same region as an absorbent layer in its gusset assembly. And, a waterproof seam tape may be used to both top and bottom edges of the gusset assembly 114 to the body fabric.

Noticeably, in FIG. 6, the shape and other characteristics of the gusset assembly in a full coverage panty may be different than other configurations/styles. For example, the wicking layer 614 of the gusset assembly may extend past the absorbent layer 612. The wicking layer 614 may include a region with a more triangular and cone-like shape that provides coverage and protection from leaks, but without an absorbent layer adjacent to it. In some examples, the aforementioned region may be simply a body fabric and wicking layer 614; in other examples, the aforementioned region is a body fabric then waterproof layer and then wicking layer 614. In the example of FIG. 6, the wicking layer 614 of the gusset assembly is cone-shaped and spans from a crotch region between the two leg opening portions all the way up to the waistband, wherein a narrowest end of the cone-shaped portion is affixed to the continuous waistband for additional structural integrity. The gusset region may be narrower in the buttock region than in the crotch region; in other words, the gusset assembly is not widely across the buttock region. In one example, the outer layer (e.g., body fabric) of the undergarment is a cotton fabric or a cotton-spandex blend fabric that is not water-resistant.

Figure 7A:
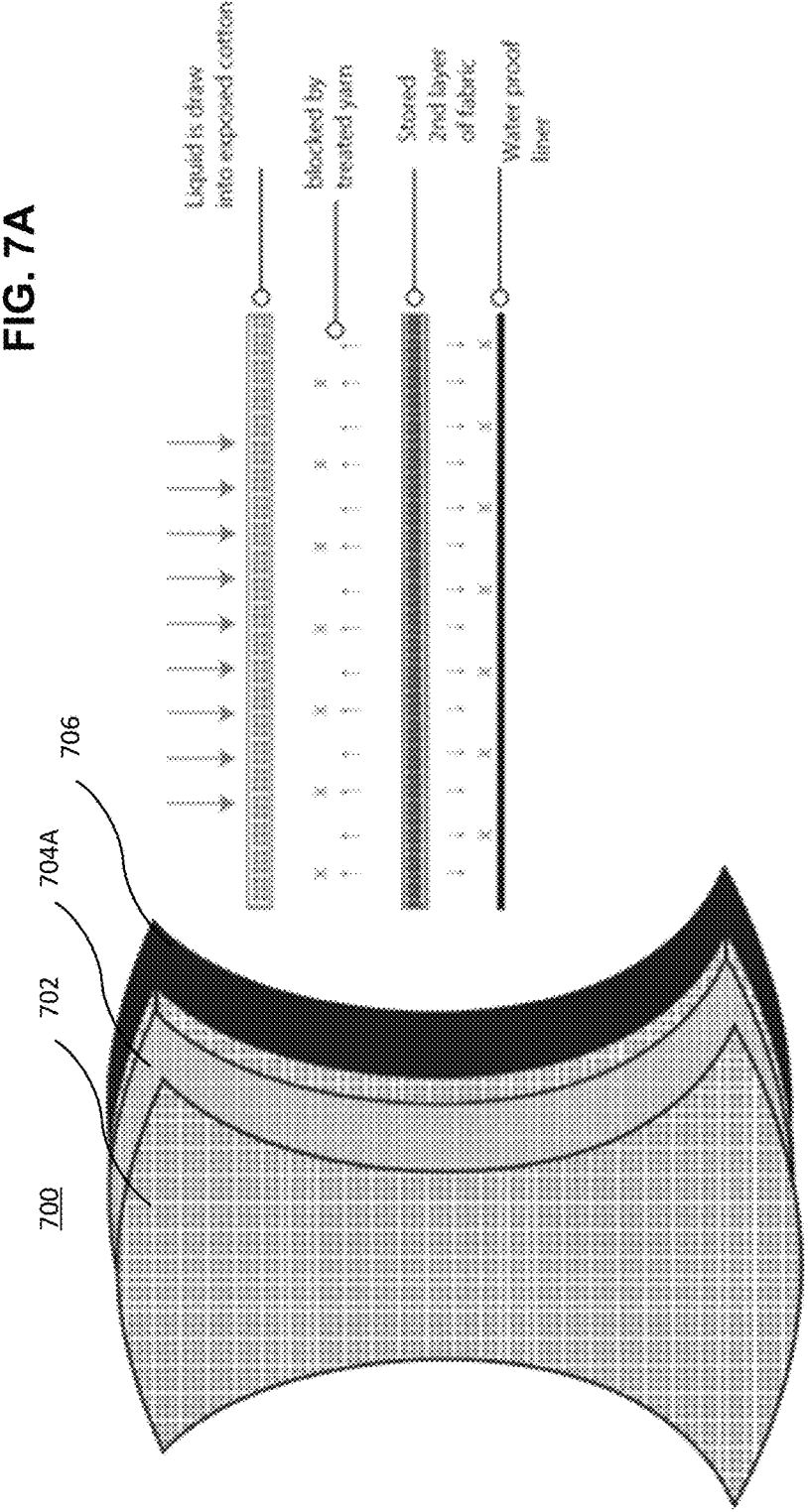
FIG. 7A and FIG. 7B (collectively referred to as "FIG. 7") show an illustrative construction of layers in a gusset assembly in an example of a reusable panty, in accordance with one or more embodiments.
Figure 7A:
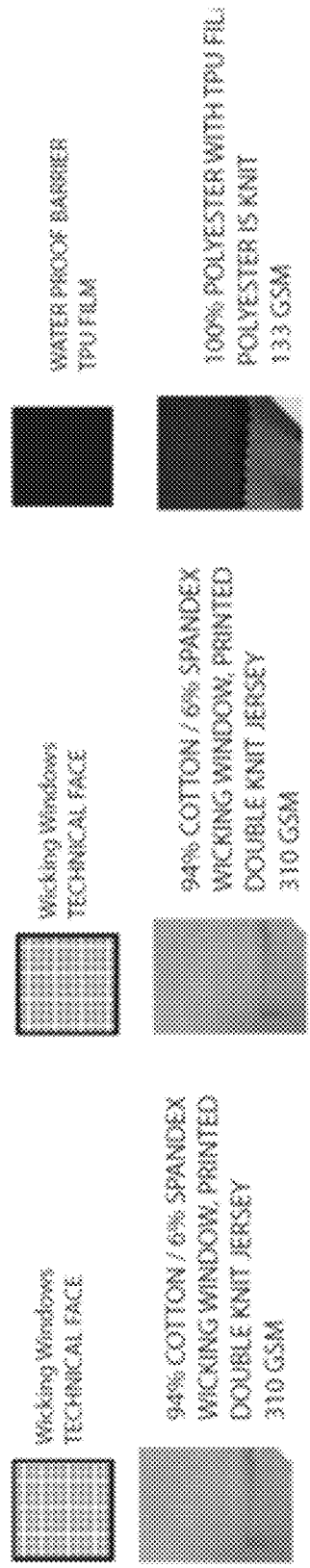
Figure 7B:
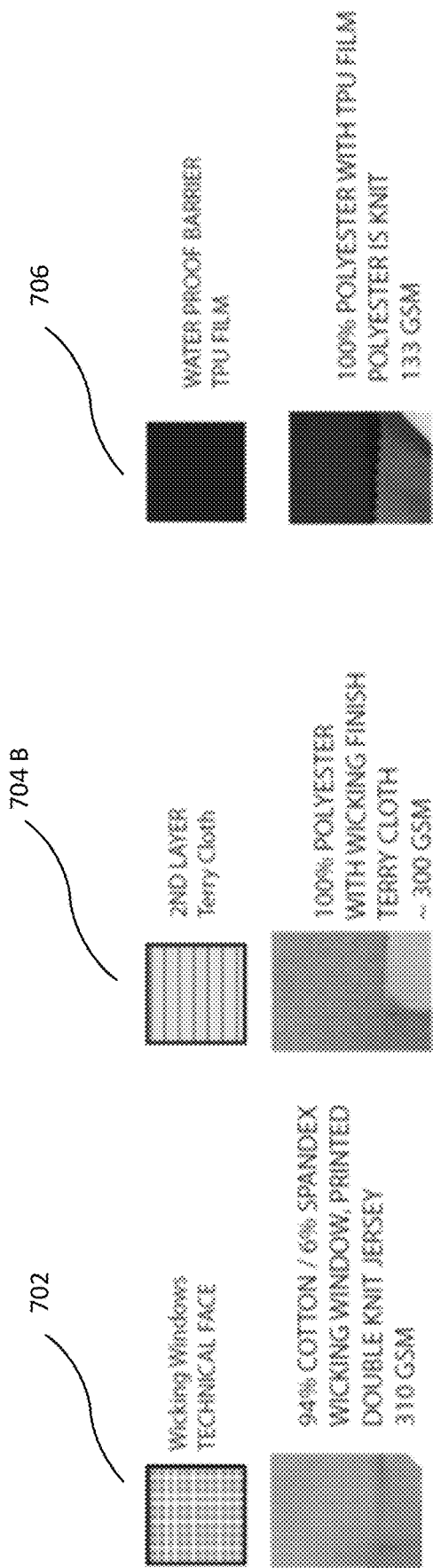

Further to the description in FIG. 6 about one or more layers of the gusset assembly, FIG. 7A and FIG. 7B (collectively referred to as "FIG. 7") show an illustrative construction of layers in a gusset assembly in one example of a reusable panty. FIG. 7A shows an illustrative construction of layers in a gusset assembly in an example of a light coverage, reusable panty, in accordance with one or more embodiments. In one example, a gusset assembly 700 may comprise one or more layers. A first layer may be a wicking layer 702 in a double-knit construction. In some examples, the wicking layer 702 may be 94% cotton and 6% spandex, wicking window, printed double-knit jersey. A second layer may be an absorbing layer 704A configured to hold and disperse liquid absorbed through the wicking layer 702. In some examples, the absorbing layer 704A may be the same fabric composition blend as the wicking layer 702 but treated with one or more agents to enhance its ability to store liquids. In another example, the absorbing layer 704A may comprise one or more sub-layers, such as two layers of woven microfiber terry cloth. A third layer may be a waterproof barrier 706. The waterproof layer 706 may be 100% knit polyester with TPU film to create a barrier to liquid absorbed by the absorbing layer 704A. In some examples, the outer body fabric of an undergarment may be considered a fourth layer that is adjacent to the third layer. In one example, the reusable panty is distinguishable from a swimsuit in that the outer body fabric of the garment is not water-resistant. Rather, if the outer body fabric comes in contact with moisture from the outside, then that fabric layer would absorb the liquid without the benefit of the gusset assembly disclosed herein.

In one example, the water-resistant layer 706 may be composed of a flexible plastic-like material that is moisture-proof or impervious, for example, polyvinyl chloride, a polyethylene film, a woven hydrophobic fabric, or some similar moisture-proof material. In one example, a gusset assembly 700 may be, for example, a pair or more of woven hydrophobic fabric sublayers with the first having its nap disposed upwardly for absorbing and wicking moisture to draw it through the interstices of the material to the opposite side where it is captured or restrained by the second sheet of hydrophobic fabric whose nap is disposed in the opposite direction so as to render it virtually moisture proof or waterproof. Such a laminate of a first and second hydrophobic sheets may be used as an outer layer or as a layer immediately inwardly adjacent thereto. In one example, the outer water-barrier layer 706 may be a relatively thin, light weight, mesh-like material of cellulose or the like. Some construction considerations include, but are not limited to, layers sewn in strategic areas of the garment or centralized in the gusset area with a waterproof barrier around the gusset and minimal/reduced visual cues from the outside of the garment. The wicking layer 702 may be made of cotton, which is a comfortable and familiar fabric for undergarments.

While many of the examples disclosed herein describe a non-removable, permanently affixed gusset assembly integrated into the undergarment, in an alternate example, an absorbent pad/layer 704A may be removable and replaceable. Moreover, the gusset assembly 700 may be treated with silver or other elemental compositions to provide anti-microbial/anti-bacterial functions; however, the gusset assembly does not use activated carbon filter for any such purpose.

FIG. 7B shows illustrative materials/fabrics for the layers in a gusset assembly in an example of a moderate coverage, reusable panty, in accordance with one or more embodiments.

The absorbent layer 704B in FIG. 7B is different from the gusset assembly 700 in FIG. 7A. Rather, the absorbent layer 704B may be 100% polyester with a wicking finish, terry cloth in one example. Moreover, in other examples, additional layers may be added to the gusset assembly to provide additional features and/or enhancements. While wicking layer 702 already has characteristics that provide for absorption of moisture, an additional wicking layer may be included to further wick and spread moisture that has entered into the wicking layer from the direction of a user wearing the undergarment, prior to reaching the absorbent layer 704B. This advantageously reduces the rate at which the absorbent layer 704B is locally saturated. For example, when liquids contact the generally same region of the gusset assembly, the absorbent layer 704B may become saturated at a localized region. With an additional wicking layer above the absorbent layer 704B, liquids/moisture may also wicked by the additional wicking layer outwards such that a volume of fluid is further spread out and can be received in a wider area of the underlying absorbent layer 704B.

Although the illustrative gusset assemblies in FIG. 7 are shown having three layers, the disclosure is not so limited. In some embodiments, the gusset assembly may comprise just two layers—e.g., a waterproof layer and an absorbent layer, but without a wicking layer. In other example, the gusset layer may be a single layer of material with a treatment applied to provide hydrophobic properties on one side while absorbent properties on the opposing side. In other examples, a layer may comprise one or more sublayers and/or agent treatments to modify the characteristics of the layer.

Figure 8:
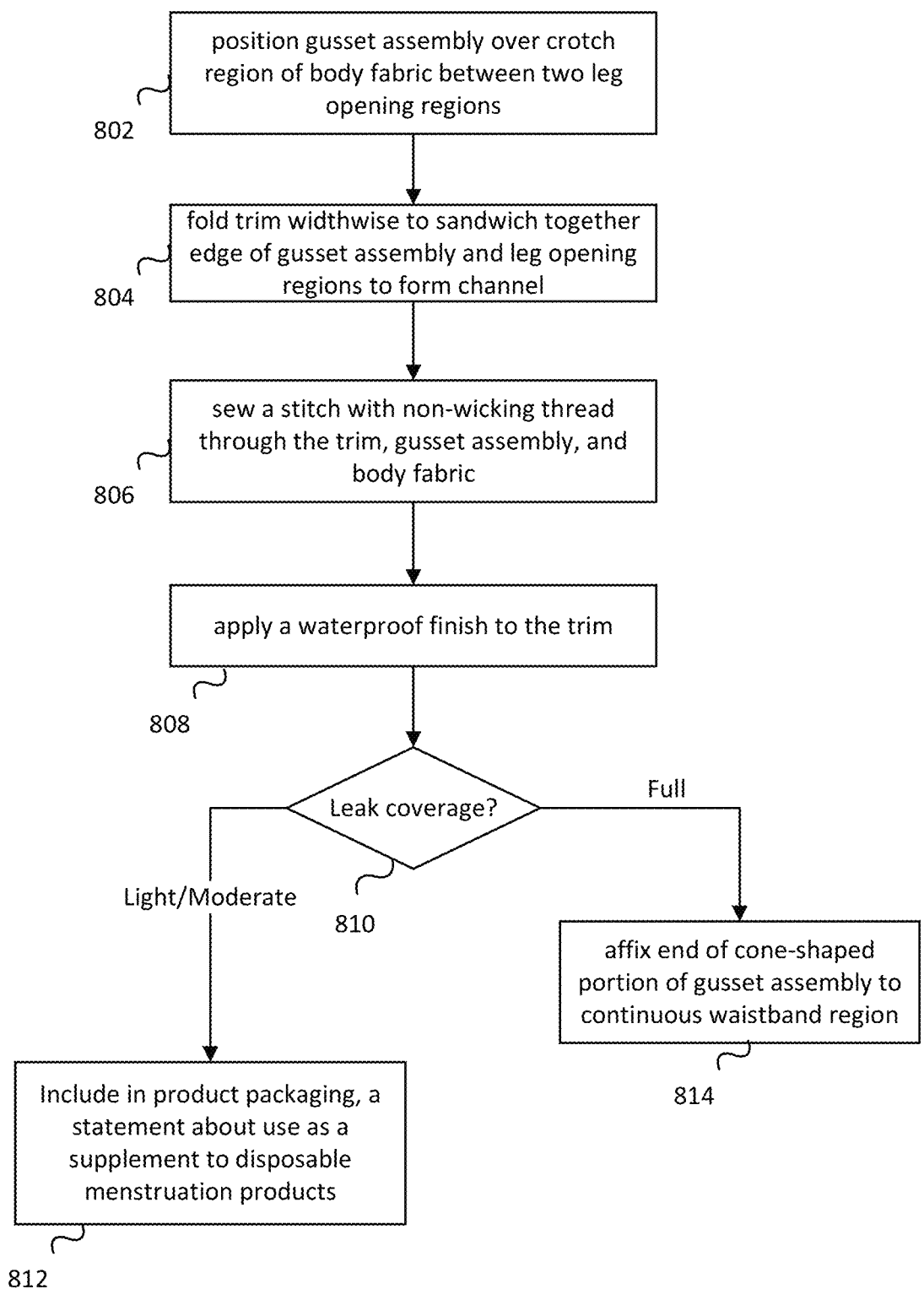
FIG. 8 is a flowchart depicting an illustrative method of manufacturing/assembling a reusable undergarment having a body layer and multi-layer gusset assembly, in accordance with one or more embodiments.

FIG. 8 is a flowchart depicting an illustrative method of manufacturing/assembling a reusable undergarment having a body layer and multi-layer gusset assembly, in accordance with one or more embodiments. Some manufacturing processes may include applying a waterproof finish to an elastic trim before sewing it onto the undergarment. The trim may be folded widthwise and positioned offset from the fold-line to an edge of the gusset assembly before affixing to the undergarment. The shape and/or positioning of the gusset assembly may be varied across different embodiments, and some examples may have a cone-shaped gusset.

FIG. 8 illustrates one example of a method of manufacturing a reusable garment that has a body layer and a gusset assembly integrated into the inside of the garment. The gusset assembly may be one layer, multi-layered, and/or include sub-layers. In one example, the gusset assembly comprises an absorbent layer, a wicking layer, and a water-resistant shield layer. In other examples, one or more of the aforementioned layers may be omitted or other layers or sub-layers may be added. The assembly/manufacturing process for the reusable garment includes positioning 802 the gusset assembly over a region (e.g., crotch region of the body fabric between two leg opening regions) of the body fabric. The water-resistant shield layer of the gusset assembly may face the body fabric and be positioned as illustrated in FIG. 7, between the body fabric and absorbent layer. In some examples, the absorbent layer may comprise 100% polyester with wicking finish terry cloth, and the body fabric might be material other than water-resistant material. In other examples the composition of the layers and/or sublayers of the gusset layer may be other materials.

In FIG. 8, the assembly/manufacturing process may further include, either manually or in an automated fashion with a machine, folding 804 a fabric (e.g., an elastic trim) widthwise to sandwich together an edge of the gusset assembly and at least one leg opening region of the body fabric. The aforementioned sandwiching may be performed by folding an elastic trim where one side of the elastic trim is on top of the gusset assembly and an opposing side of the elastic trim is on bottom of the gusset assembly. The trim is sufficiently wide before being folded so that it can function as a hollow channel for liquid. In one example, the trim is at least one-half inch in width before folded widthwise. The folding may create an at least partially hollow channel within the trim that functions to, among other things, redistribute/spread any liquid or moisture excreted at the edges of the gusset assembly. The folded trim need not necessarily be folded with a crease; rather, the trim may be folded in any way that allows one side of the trim to be on top of the gusset assembly and the other side of the trim on the bottom side of the gusset assembly (e.g., the portion of the gusset assembly adjacent the outer body fabric). In one example, the folded trim may be un-creased when assembled and form a circular-like shape.

The assembly/manufacturing process of FIG. 8 may further include sewing 806 a stitch with non-wicking thread through at least the one side of the elastic trim, the opposing side of the elastic trim, the gusset assembly, and the leg opening regions of the body fabric. Any of numerous types of stitches may be used in step 806; in one example, a two-needle cover stitch is sewn that is visible as two parallel stitch lines on the one side of the elastic trim. In other examples, one or more of the numerous other stitches described herein may be used in step 806. Although FIG. 8 illustrates step 806, that step is not required in all embodiments contemplated by this disclosure. In one example, to manufacture an alternate, full coverage undergarment, the manufacturing process may occur without any stitching of the trim; rather, the internal cone-shaped portion of the gusset assembly for full coverage and the folded trim may be bonded using other techniques. Meanwhile, the narrow end of the cone-shaped portion of the gusset assembly may be further bonded to a waistband of the undergarment. Likewise, one or more other steps illustrated in FIG. 8 may be optional and/or performed in orders others than depicted in FIG. 8 for illustration purposes.

In addition, to prevent leakage from the edges of the garment, a finish (e.g., a waterproof finish or any other agent/treatment that resist the passage of liquid) may be applied 808 to the trim. Although FIG. 8 illustrates step 808 as occurring after step 804 in the flowchart, a person skilled in the art after review of the entirety disclosed herein will recognize that the disclosure is not so limited. For example, in some assembling processes in accordance with the embodiments disclosed herein, a treatment may be first applied 808 to a trim, and the pre-treated trim may be then folded 804 and sewn 806 at a later time to the body fabric. In other examples, step 808 may be performed after steps 804 and 806 so that the application of any waterproof finish to the trim may also enhance any non-wicking thread that may have been stitched in step 806 through the trim and other fabrics.

In FIG. 8, step 810, the assembly/manufacturing process may depend on the configuration/style of the garment being produced. For example, for a full coverage undergarment, the overall gusset assembly may include a cone-shaped portion. The cone-shaped portion may be positioned during assembly to span from the crotch region between the two legs opening regions to a continuous waistband region (e.g., the waistband) of the undergarment. The narrowest end of the cone-shaped portion may be affixed 814 to the continuous waistband region. In some embodiments, the gusset assembly may be affixed to a region other than the continuous waistband—e.g., to a region at a location under the waistband—but at least one benefit of attaching to the waistband is increased structural integrity for the overall garment.

In some examples, when the assembly/manufacturing process is for an undergarment with light and/or moderate coverage, the gusset assembly might not be as noticeably cone-shaped in appearance and structure. Rather, the product packaging in which the undergarment is provided may include 812 a statement or indication the use of the undergarment as a supplement to existing disposable products (e.g., disposable menstruation products, disposable incontinence products, or other comparable disposables).

Some embodiments disclosed herein provide absorbent and leak-proof intimate apparel while solving for concerns around discretion and comfort. For example, some embodiments deal with leakages resulting from stress incontinence that results from unintentional urine in men and women during physical activity, coughing/sneezing, or even laughing. In addition, some embodiments deal with leakages resulting from female menstruation. Of course, in the aforementioned examples, the placement of a gusset assembly in the crotch region may be adjusted to accommodate for differences in the location of emission of urine from the urethra compared to the location of menstrual fluids/liquids excreted from the vagina. The gusset assembly may be positioned farther forward or backwards in the crotch region of a panty undergarment to accommodate the aforementioned implementations. In another example, the gusset assembly may be specifically shaped to cover specific parts of the crotch region of a panty undergarment to accommodate the aforementioned implementations.

Throughout the application, it should be noted that the terms "first," "second," and the like herein do not denote any order or importance, but rather are used to distinguish one element from another, and the terms "a" and "an" herein do not denote a limitation of quantity, but rather denote the presence of at least one of the referenced items. Similarly, it is noted that the terms "bottom" and "top" are used herein, unless otherwise noted, merely for convenience of description, and are not limited to any one position or spatial orientation. In addition, the modifier "about" used in connection with a quantity is inclusive of the stated value and has the meaning dictated by the context (e.g., includes the degree of error associated with measurement of the particular quantity).

While aspects of the disclosure have been described in terms of illustrative embodiments thereof, it should be understood by those skilled in the art that various changes may be made and equivalents may be substituted for elements thereof without departing from the scope of the disclosure. Numerous other embodiments, modifications, and variations within the scope and spirit of the appended claims will occur to persons of ordinary skill in the art from a review of this disclosure. For example, one or more of the steps depicted in the illustrative figures may be performed in other than the recited order, and one or more depicted steps may be optional in accordance with aspects of the disclosure.

What is claimed is:

1. A reusable undergarment comprising:
    a body fabric comprising a continuous waistband and two leg opening portions;
    a gusset assembly comprising more than two layers, wherein the gusset assembly is positioned inside the undergarment and includes at least an absorbent layer, wicking layer, and water-resistant shield layer;
    a first bi-fold, elastic trim sandwiching a first of the two leg opening portions of the body fabric and a first edge of the gusset assembly between a first side of the first bi-fold, elastic trim and a second side of the first bi-fold, elastic trim;
    a second bi-fold, elastic trim sandwiching a second of the two leg opening portions of the body fabric, and a second edge of the gusset assembly, wherein the second edge of the gusset assembly is opposite the first edge of the gusset assembly between a first side of the second bi-fold, elastic trim and a second side of the second bi-fold, elastic trim;
    a first non-wicking, hydrophobic thread sewn through the first bi-fold trim, all of the two or more layers of the gusset assembly, and the body fabric to form the sandwiching by the first bi-fold trim; and
    a second non-wicking, hydrophobic thread sewn through the second bi-fold trim, all of the two or more layers of the gusset assembly to form the sandwiching by the second bi-fold trim, and the body fabric, wherein the first thread and the second thread are separate threads, wherein the gusset assembly is permanently affixed in the undergarment to absorb liquids excreted by a wearer of the undergarment and is reusable after washing.

2. The undergarment of claim 1, wherein the first bi-fold, elastic trim is a single piece of fabric with a waterproof finish, and wherein the first bi-fold, elastic trim is folded widthwise to form a channel to collect and redistribute excess liquid at the first edge of the gusset assembly without leaking out onto an outer apparel of the wearer of the undergarment.

3. The undergarment of claim 1, wherein the first non-wicking, hydrophobic thread forms a two-needle cover stitch.

4. The undergarment of claim 3, wherein the two-needle cover stitch is visible as two parallel stitch lines on an external-facing side of the first bi-fold, elastic trim.

5. The undergarment of claim 3, wherein the sandwiching by the first bi-fold, elastic trim is done in the absence of any of chemical bonding, elastic bonding film, thermal-compression bonding, or combination thereof.

6. The undergarment of claim 1, wherein the first bi-fold, elastic trim comprises a single piece of water-resistant fabric that is at least one-half inch in width before folded widthwise.

7. The undergarment of claim 2, wherein the first edge of the gusset assembly is positioned to be offset by a distance from a fold-line of the first bi-fold, elastic trim when folded widthwise to form a channel to collect and redistribute any excess liquid.

8. The undergarment of claim 1, wherein the wicking layer of the gusset assembly is designed to absorb moisture received from the wearer.

9. The undergarment of claim 1, wherein the water-resistant shield layer is in direct contact with the body fabric, and the wicking layer is positioned to be in direct contact with a skin of a wearer of the undergarment, and the absorbent layer is positioned between the wicking layer and the water-resistant shield layer.

10. The undergarment of claim 1, wherein the absorbent layer comprises 100% polyester with wicking finish terry cloth, and wherein the body fabric is not water-resistant.

11. The undergarment of claim 1, wherein the gusset assembly comprises a cone-shaped portion spanning from a crotch region between the two leg opening portions to the continuous waistband, wherein a narrowest end of the cone-shaped portion contacts the continuous waistband.

12. The undergarment of claim 1, wherein the gusset assembly is positioned in the crotch region with more coverage towards a center and back of the crotch region than the front of the crotch region, and wherein the undergarment includes product packaging marketing it as a supplement to disposable menstruation products.

13. The undergarment of claim 1, wherein the body fabric in contact with the first bi-fold, elastic trim is void of any visible pleats or folds in the body fabric running generally perpendicular to the trim.

14. A reusable undergarment comprising:
    a body fabric comprising a continuous waistband and two leg opening portions;
    a gusset assembly comprising two or more layers, wherein the gusset assembly is positioned inside the undergarment;
    an elastic trim folded widthwise to sandwich a first of the two leg opening portions of the body fabric and an edge of the gusset assembly between a first side of the elastic trim and a second side of the elastic trim to form a hollow channel that redistributes excess liquid at the edge of the gusset assembly without leaking out onto an outer apparel of a wearer of the undergarment; and
    a non-wicking, hydrophobic thread sewn with a two-needle cover stitch through the trim, all of the two or more layers of the gusset assembly, and the body fabric to form the sandwiching by the trim without aid of any of chemical bonding, elastic bonding film, thermal-compression bonding, or combination thereof;
    wherein the two-needle cover stitch is visible as two parallel stitch lines on the trim,
    wherein the elastic trim is a single piece of fabric with a waterproof finish,
    wherein the gusset assembly is permanently affixed in the undergarment to absorb liquids excreted by the wearer of the undergarment and is reusable after washing.

15. The undergarment of claim 14, wherein the trim is at least one-half inch in width before folded widthwise.

16. The undergarment of claim 14, wherein the gusset assembly includes at least an absorbent layer, wicking layer, and water-resistant shield layer, and wherein the water-resistant shield layer is in direct contact with the body fabric, and the wicking layer is positioned to be in direct contact with a skin of the wearer of the undergarment, and the absorbent layer is positioned between the wicking layer and the water-resistant shield layer, and wherein the body fabric is not water-resistant.

17. The undergarment of claim 14, wherein the edge of the gusset assembly is positioned to be offset by a distance from a fold-line of the trim when folded widthwise, and wherein the gusset assembly comprises a cone-shaped portion spanning from a crotch region between the two leg opening portions to the continuous waistband, wherein a narrowest end of the cone-shaped portion contacts the continuous waistband.

18. A method of manufacturing a reusable garment comprising a body fabric and a gusset assembly overlying the body fabric, the gusset assembly comprising an absorbent layer, a wicking layer, and a water-resistant shield layer, the method comprising:

positioning the gusset assembly over at least a crotch region of the body fabric between two leg opening regions of the body fabric with the water-resistant shield layer of the gusset assembly facing the body fabric and being between the body fabric and the absorbent layer;

folding an elastic trim widthwise to sandwich together an edge of the gusset assembly and at least one leg opening region of the body fabric, wherein one side of the elastic trim is on top of the gusset assembly and an opposing side of the elastic trim is on bottom of the gusset assembly and the at least one leg opening region of the body fabric is also between the opposing sides of the elastic trim, and wherein the folded elastic trim creates an at least partially hollow channel to redistribute liquid excreted at the edge of the gusset assembly;

sewing a stitch with non-wicking thread through at least the one side of the elastic trim, the opposing side of the elastic trim, the gusset assembly, and the body fabric; and applying a waterproof finish to the elastic trim;

wherein the reusable garment is configured to be washed then re-worn numerous times.

19. The method of manufacturing of claim 18, wherein the gusset assembly comprises a cone-shaped portion spanning from the crotch region between the two leg opening regions to a continuous waistband region of the body fabric, the method further comprising:

affixing a narrowest end of the cone-shaped portion to the continuous waistband region.

20. The method of manufacturing of claim 18, wherein the absorbent layer comprises 100% polyester with wicking finish terry cloth, and wherein the body fabric is not water-resistant, and wherein the stitch comprises a two-needle cover stitch that is visible as two parallel stitch lines on the one side of the elastic trim, and wherein the reusable garment is an undergarment.

* * * * *